United States Patent [19]

Takahashi et al.

[11] Patent Number: 4,794,115

[45] Date of Patent: Dec. 27, 1988

[54] METHOD OF TREATING HYPERLIPEMIA

[75] Inventors: Keiko Takahashi, Tsuchiura; Toshio Wakabayashi, Tama, both of Japan

[73] Assignee: Terumo Corporation, Tokyo, Japan

[21] Appl. No.: 925,239

[22] Filed: Oct. 31, 1986

[30] Foreign Application Priority Data

Nov. 1, 1985 [JP] Japan ................................ 60-245794

[51] Int. Cl.$^4$ ............................................ A61K 31/44
[52] U.S. Cl. .................................................... 514/356
[58] Field of Search .................. 436/71; 546/348, 318; 514/356

[56] References Cited

PUBLICATIONS

Takahashi et al., Chem. Abst. 107:39501s (1987), abstracting Belgian Patent No. 901,987 issued Jul. 16, 1985.

Seki et al., "Studies on Hypolipidemic Agents I. Synthesis and Pharmacological Properties of Nicotinic Acid–Ethanolamine Derivatives", *Chem. Pharm. Bull* 31(11) 4116–4126 (1983).

*Primary Examiner*—Allen J. Robinson
*Assistant Examiner*—Richard Kearse
*Attorney, Agent, or Firm*—Cushman, Darby & Cushman

[57] ABSTRACT

A method of treating or preventing hyperlipemia by administering ethanolamine derivatives. As preferable ethanolamine derivatives are mentioned N-(9,12,15,-octadecatrienoyl)-2-aminoethyl nicotinate, N-(5,8,11,14,17-eicosapentaenoyl)-2-aminoethyl nicotinate and the like. Hyperlipemia is effectively prevented or treated by administering 300–2000 mg per day of said ethanolamine derivative for adults.

9 Claims, No Drawings

METHOD OF TREATING HYPERLIPEMIA

BACKGROUND OF THE INVENTION

1. Field of the Invention

The present invention relates to a method of treating hyperlipemia.

More particularly, the invention is concerned with a treating or preventing method of hyperlipemia by administering an ethanolamine derivative to mammals acutually or potentially afflicted with hyperlipemia.

Hyperlipemia is a disease with turbid serum and increased blood level of triglycerides associated which will cause myocardial infarction and cerebral blockade. Therefore, treatment of hyperlipemia is important in the prevention of such diseases.

2. Description of the Prior Arts

A variety of drugs have heretofore been known as the antihyperlipemic agent. However, as effects of the known agents are not satisfactory, development of more effective agents has been desired.

SUMMARY OF THE INVENTION

The present invention is concerned with a method of treating or preventing hyperlipemia which comprises administering mammals (including human beings) actually or potentially suffering from hyperlipemia with an effective dose of an ethanolamine derivative represented by the general formula

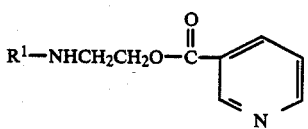

wherein $R^1$ represents a hydrogen atom or an acyl group derived from a trienoic higher fatty acid or eicosapentaenoic acid.

DETAILED DESCRIPTION OF THE INVENTION

We have previously prepared a variety of ethanolamine derivatives and extensively investigated their pharmacological activities and found that the above ethanolamine derivatives possess potent platelet aggregation inhibitory activity and filed patent application (U.S. Pat. Appln. 713,496, now U.S. Pat. No. 4,619,938; European Pat. Publn. No. 161,422). As a result of further studies, we have found that the ethanolamine derivatives have also potent antihyperlipemic activities. The present invention has been completed on the basis of the above finding.

It is an object of the invention to provide a method of treating or preventing hyperlipemia by administering a potent antihyperlipemic agent containing an ethanolamine derivative represented by the above-described formula (I).

The ethanolamine derivatives employed in the invention possess distinguished serum lipid-lowering activities and are useful as prophylactic agents for arteriosclerosis caused by high serum lipid. $R^1$ in the above-described formula (I) represents either a hydrogen atom, or preferably an acyl group derived from trienoic higher fatty acids or eicosapentaenoic acid. As the trienoic higher fatty acid is preferred α- or γ-linolenic acid.

The ethanolamine derivatives employed as the active principle or one of the active principles have potent serum lipid-lowering activities. Said derivatives of the invention effectively act upon any diseases caused by hyperlipemia in which serum cholesterol or serum triglycerides are higher. Especially they are useful prophylactic agent for arteriosclerosis, myocardial infarction or cerebral blockade. The daily dose is, in ggeneral, in the range between 300 and 2000 mg for adults divided, as needed, into 1 to 3 doses. The method of administration may be in any form suitable for the administration, and oral administration is desirable. Intravenous administration is also feasible.

The above-mentioned compounds, used in the invention, alone or in admixture with carriers or excipients as in a conventional way, are prepared into tablets, powders, capsules or granules. Examples of the carrier or excipient include calcium carbonate, calcium phosphate, starch, sucrose, lactose, talc, magnesium stearate and the like. In addition to the above-mentioned solid preparations, liquid preparations such as oily suspension or syrup may be prepared.

The above-mentioned compounds may also be used in the invention after stabilized by the inclusion with dextrin.

The ethanolamine derivatives of the present invention are prepared by processes known per se. For example in cases where $R^1$ is acyl group as defined above, a trienoic higher fatty acid or eicosapentaenoic acid, or a reactive derivative thereof is condensed with an ethanolamine to produce an acylated ethanolamine, which is then condensed with nicotinic acid to give the ethanolamine derivatives (I).

As a condensing agent in the condensation of a fatty acid with an ethanolamine is preferably employed ethyl chloroformate, for example. As examples of the reactive derivative of the fatty acids may be mentioned carboxylic acid chlorides and thiazolidinethionamide derivatives of the carboxylic acid.

In the condensation of the acylated ethanolamine with nicotinic acid, a condensing agent such as, for example, N,N-dicyclohexylcarbodiimide, 2-chloro-1-methylpyridinium or a p-toluenesulfonate is employed. It is preferred to carry out both of the reactions in the steps 1 and 2 under inert gas such as argon. After completion of the reaction, the reaction product is isolated from the reaction mixture in a conventional manner and purified by such means as column chromatography.

Examples and Test Examples are given below to describe the invention in more details.

EXAMPLE 1

To a solution of 1.000 g of 9,12,15-octadecatrienoic acid in 20 ml of dry chloroform at room temperature was added in the atmosphere of argon 0.50 ml of oxalyl chloride. The mixture was reacted for 2 hours. From the reaction mixture were removed the chloroform and the remaining oxalyl chloride by distillation. The 9,12,15-octadecatrienoyl chloride thus produced was again dissolved in 2 ml of dry chloroform.

Separately, to a solution of 1.090 g of ethanolamine in 20 ml of dry chloroform was added in the atmosphere of argon 990 mg of anhydrous potassium carbonate. To the mixture at room temperature was added the chloroform solution of 9,12,15-octadecatrienoyl chloride prepared above, followed by reaction for 30 min. From the reaction mixture was removed insoluble matters by filtration. To the mother liquor was added water, and the mixture was extracted three times with chloroform.

The organic layer from the extraction was washed with water and dried over anhydrous sodium sulfate, and the solvent was removed by distillation under reduced pressure. There was obtained 1.20 g of residue, which was subjected to silica gel column chromatography. From a fraction eluted with chloroform-methanol (98:2) was obtained 1.045 g of N-(9,12,15-octadecatrienoyl)-2-aminoethanol. Then, to a solution of 1.000 g of said compound in 40 ml of dry chloroform at room temperature were added in the atmosphere of argon 709 mg of nicotinoyl chloride hydrochloride and subsequently 1.691 g of anhydrous potassium carbonate, followed by reaction overnight. From the reaction mixture was removed insoluble matters by filtration. To the mother liquor was added water, and the mixture was neutralized with 1N aqueous solution of lithium hydroxide and then extracted three times with chloroform. The extract was washed with water. The organic layer from the extraction was dried over anhydrous sodium sulfate, and then the solvent was removed by distillation under reduced pressure. There was produced 1.402 g of extraction residue, which was subjected to silica gel column chromatography. From fractions eluted with chloroform to chloroform-methanol (98:2) was obtained 1.075 g of N-(9,12,15-octadecatrienoyl)-2-aminoethyl nicotinate. Physicochemical data of the product supports the structure (II) shown below.

IR$\nu_{max}^{CHCl_3}$ (cm$^{-1}$): 3460, 1725, 1675, 1595, 1515.

$^1$H-NMR(CDCl$_3$) δ (ppm): 0.94(3H, t, J=7.5 Hz), 3.63(2H, q, J=5.5 Hz), 4.48(2H, t, J=5.5 Hz), 7.32(1H, dd, J=8 Hz, 5 Hz), 8.22(1H, dt, J=8 Hz, 2 Hz), 8.75(1H, dd, J=5 Hz, 2 Hz), 9.25(1H, d, J=2 Hz).

mass(m/e): 426 (molecular ion peak), 303, 106.

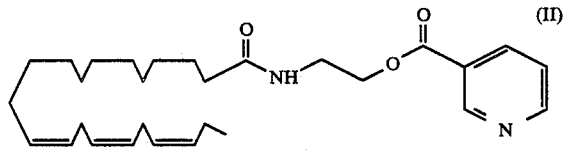

EXAMPLE 2

To a tetrafuran (10 ml) solution of 5,8,11,14,17-eicosapentaenoyl thiazolidinethionamide (500 mg, 1.24 mmol) was added in an atmosphere of argon at room temperature a tetrahydrofuran (1.5 ml) solution of 84 mg (1.3 mmol) of 2-aminoethanol. The mixture was reacted for 20 min. followed by addition of 10 ml of 1N aqueous solution of sodium hydroxide and extraction with three portions of dichloromethane. The organic layer from the extraction was washed with water and dried over anhydrous sodium sulfate. The solvent was then removed by distillation under reduced pressure to yield 437 mg of residue. The residue was subjected to silica gel column chromatography. From a fraction eluted with chloroform-methanol (95:5) was obtained 356 mg (1.03 mmol) of N-(5,8,11,14,17-eicosapentaenoyl)-2-aminoethanol.

To a solution of 77 mg (0.63 mmol) of nicotinic acid in a mixed solvent of tetrahydrofuran (2 ml) and 1,2-dichloroethane (2 ml) at room temperature were successively added in an atmosphere of argon 7 mg (0.06 mmol) of 4-dimethylaminopyridine, 129 mg (0.63 mmol) of N,N'-dicyclohexylcarbodiimide and 196 mg (0.57 mmol) of N-5,8,11,14,17-eicosapentaenoyl-2-aminoethanol, which were dissolved in 1,2-dichloroethane (1.5 ml), respectively. The mixture was reacted overnight, and precipitates then produced were separated by filtration and washed with benzene. To the mother liquor was added water, and the mixture was extracted three times with dichloromethane. The organic layer from the extraction was washed with water and dried over anhydrous sodium sulfate. The solvent was then removed by distillation under reduced pressure to give 311 mg of extraction residue, which was subjected to silica gel column chromatography. From a fraction eluted with chloroform-methanol (98:2) was obtained 246 mg (0.55 mmol) of N-(5,8,11,14,17-eicosapentaenoyl)-2-aminoethyl nicotinate. Physicochemical properties of the product supports the formula (III) shown below.

IR$\nu_{max}^{CHCl_3}$ (cm$^{-1}$): 3425, 1725, 1665, 1580, 1495.

$^1$H-NMR (CDCl$_3$) δ: 0.93(3H, t, J=7.5 Hz), 3.67(2H, q, J=5.5 Hz), 4.43(2H, t, J=5.5 Hz), 7.36(1H, dd, J=8 Hz, 5 Hz), 8.28(1H, dt, J=8 Hz, 2 Hz), 8.77(1H, dd, J=5 Hz, 2 Hz,), 9.18(1H, bd, =2 Hz).

mass(m/e): 450 (molecular ion peak), 381, 106, 78.

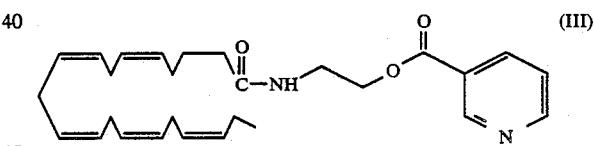

TEST EXAMPLE

Wistar-King male rats weighing 170 g are orally administered with 5% acacia gum suspension of the compound obtained in Example 1 or 2. Thirty minutes thereafter, a mixture of 10% cholesterol, 1% cholic acid and corn oil is orally administered at a dose of 10 ml/kg.

The above-described administration is made once a day for consecutive 7 days, and 4 hours after the last administration blood is drawn from the abdominal large artery of the rats under ether anesthesia. The blood is centrifuged at 1630×g at 4° C. for 10 min. to isolate serum. Measurements were made on serum levels of total cholesterol and triglycerides by means of serum lipid reagents, V-cholestase (Nissui, trade name for the total cholesterol) and V-Triglase (Nissui, trade name for the triglycerides). Results are shown in Table 1, in which mean values for a group of 6 animals are shown.

TABLE 1

| Structural formula | Ex. No. | R[1] | Dose (mM/kg) | Serum lipid level (mg/dl) | |
|---|---|---|---|---|---|
| | | | | Total cholesterol | Triglyceride |
| R[1]—N—CH₂CH₂—O—C(=O)—(pyridine) H | 1 | (octadecatrienoyl acyl, C(=O)–chain) | 1.2 2.4 | 198.9 146.6 | 350.1 258.4 |
| | 2 | (eicosapentaenoyl acyl chain) | 1.2 2.4 | 194.8 130.4 | 296.4 202.8 |
| Nicotinic acid HO—C(=O)—(pyridine) | Comp. | — | 2.4 | 195.4 | 312.2 |
| Control | — | — | — | 210.0 | 621.7 |

Acute Toxicity

An acute toxicity test was run by oral administration using ICR male mice of 5 weeks old. LD₅₀ values for all of the compounds used in the invention were 4 g/kg or higher thereby indicating high safety.

What is claimed is:

1. A method for treating hyperlipemia in mammals in need of such treatment which comprises administering to said mammal an effective amount of an ethanolamine derivative represented by the formula

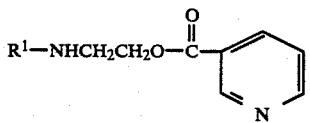

(I)

wherein R[1] represents an acyl group derived from α- or γ-linolenic acid or eicosapentaenoic acid.

2. The method of claim 1 wherein the mammal is a human being and the effective amount is 300–2000 mg per day for an adult.

3. The method of claim 1 wherein the ethanolamine derivative is administered in admixture with a carrier or excipient.

4. The method of claim 2 wherein the ethanolamine derivative is administered in admixture with a carrier or excipient.

5. The method of claim 1 wherein the ethanolamine derivative is N-(9,12,15-octadecatrienoyl)-2-aminoethyl nicotinate.

6. The method of claim 2 wherein the ethanolamine derivative is N-(9,12,15-octadecatrienoyl)-2-aminoethyl nicotinate.

7. The method of claim 1 wherein the ethanolamine derivative is N-(5,8,11,14,17-eicosapentaenoyl)-2-aminoethyl nicotinate.

8. The method of claim 2 wherein the ethanolamine derivative is N-(5,8,11,14,17-eicosapentaenoyl)-2-aminoethyl nicotinate.

9. A method for treating hyperlipemia in humans in need of such treatment which comprises administering to said human an effective amount of an ethanolamine derivative represented by the formula wherein R[1] represents an acyl group derived from α- or γ-linolenic acid or eicosapentaenoic acid and wherein the effective amount is 300–2000 mg per day for an adult.

* * * * *